United States Patent [19]

Maurer et al.

[11] Patent Number: 4,769,364

[45] Date of Patent: Sep. 6, 1988

[54] PYRIMIDIN-5-YL PHOSPHORIC ACID ESTER AND THIONOPHOSPHORIC ACID ESTER PESTICIDES

[75] Inventors: Fritz Maurer, Wuppertal; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 886,283

[22] Filed: Jul. 15, 1986

[30] Foreign Application Priority Data

Aug. 2, 1985 [DE] Fed. Rep. of Germany ....... 3527861

[51] Int. Cl.$^4$ ........................ A01N 57/16; C07F 9/65
[52] U.S. Cl. ..................................... 514/86; 544/243; 558/202; 558/204
[58] Field of Search .......................... 544/243; 514/86; 558/202, 204

[56] References Cited

U.S. PATENT DOCUMENTS 4,182,733  1/1980  Arlt ................................. 558/202 X
4,558,039 12/1985  Reifschneider et al. ............. 514/86

Primary Examiner—Donald G. Daus
Assistant Examiner—Diana G. Rivers
Attorney, Agent, or Firm—Sprung Horn Kramer & Woods

[57] ABSTRACT

Pesticidally active novel phosphates of the formula

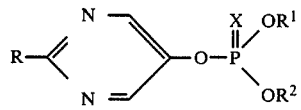

in which
R represents hydrogen, alkyl, cycloalkyl, alkoxy, alkylthio, alkylamino, dialkylamino or aryl,
$R^1$ represents alkyl,
$R^2$ represents fluoroalkyl and
X represents oxygen or sulphur.

The acid halides of the formula

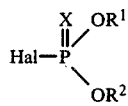

are also new.

11 Claims, No Drawings

PYRIMIDIN-5-YL PHOSPHORIC ACID ESTER AND THIONOPHOSPHORIC ACID ESTER PESTICIDES

The invention relates to new pyrimidin-5-yl-thionophosphoric acid esters, a process for their preparation and their use in agents for combating pests, in particular as insecticides and nematicides.

It is known that certain thionophosphoric acid esters, such as, for example, O-ethyl O-n-propyl O-(2-i-propyl-pyrimidin-5-yl) and O,O-diethyl O-(2-tert.-butylpyrimidin-5-yl)thionophosphate (compare, for example, U.S. Pat. No. 4,127,652 and U.S. Pat. No. 4,429,125), have very good insecticidal and nematicidal properties.

New pyrimidin-5-yl-thionophosphoric acid esters of the formula (I)

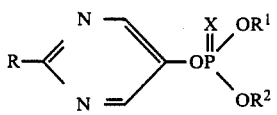

in which
R represents hydrogen, alkyl, cycloalkyl, alkoxy, alkylthio, alkylamino, dialkylamino or aryl,
$R^1$ represents alkyl,
$R^2$ represents fluoroalkyl and
X represents oxygen or sulphur,
have now been found.

It has furthermore been found that the new substituted pyrimidin-5-yl-thionophosphoric acid esters of the formula (I) are obtained by a process in which 5-hydroxypyrimidines of the formula (II)

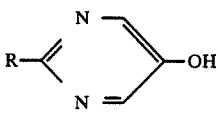

in which
R has the abovementioned meaning,
or the corresponding alkali metal, alkaline earth metal or ammonium salts, are reacted with halides of the formula (III)

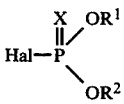

in which
X, $R^1$ and $R^2$ have the abovementioned meanings and Hal represents halogen,
if appropriate in the presence of an acid acceptor and if appropriate in the presence of a diluent.

Surprisingly, the new pyrimidin-5-yl-thionophosphoric acid esters of the formula (I) are distinguished by a particularly low toxicity and a very good nematicidal and insecticidal action.

The alkyl radicals R and $R^1$ and the alkyl parts of the alkoxy, alkylthio, alkylamino and dialkylamino radicals R can be branched or straight-chain and preferably contain in each case 1 to 8, in particular 1 to 6 and particularly preferably 1 to 4 carbon atoms. Examples which may be mentioned are: methyl, ethyl, n-propyl, isopropyl, n-butyl, iso-butyl, sec.-butyl, tert.-butyl, methoxy, ethoxy, n-propoxy, iso-propoxy, n-butoxy, sec.-butoxy, iso-butoxy, tert.-butoxy, methylthio, ethylthio n-propylthio, iso-propylthio, n-butylthio, iso-butylthio, sec.-butylthio, tert.-butylthio, (di)methylamino, (di)ethylamino, (di)n-propylamino, (di)iso-propylamino, (di)n-butylamino, (di)iso-butylamino, (di)sec.-butylamino and (di)tert.-butylamino, methylethylamino and methyl-n-propylamino.

The cycloalkyl radicals R contain 3 to 8, preferably 3 to 6, carbon atoms. Examples which may be mentioned are cyclopropyl, cyclobutyl, cyclopentyl and cyclohexyl.

The aryl radical R preferably contains 6 to 10 carbon atoms in the aryl part. Examples which may be mentioned are: naphthyl and phenyl, in particular phenyl.

The fluoroalkyl radical $R^2$ can be branched or straight-chain and preferably contains 1 to 8, in particular 1 to 6 and particularly preferably 1 to 4, carbon atoms and 1 to 8, preferably 1 to 6 and particularly preferably 1 to 4, fluorine atoms. Examples which may be mentioned are: trifluoromethyl, 2,2,2-trifluoroethyl, difluoroethyl, 3,3,3-trifluoro-1-propyl, 2,2,3,3-tetrafluoro-1-propyl, 1,1,1,3,3,3-hexafluoro-2-propyl, 2-trifluoromethyl-2-propyl and 2,2,3,4,4,4-hexafluoro-1-butyl.

X preferably represents sulphur.

The invention preferably relates to compounds of the formula (I) in which
R represents hydrogen, or represents $C_1$-$C_6$-alkyl, $C_3$-$C_6$-cycloalkyl, $C_1$-$C_6$-alkoxy, $C_1$-$C_6$-alkylthio, $C_1$-$C_6$-alkylamino, di-($C_1$-$C_4$-alkyl)amino or phenyl,
$R^1$ represents $C_1$-$C_6$-alkyl,
$R^2$ represents fluoro-$C_1$-$C_6$-alkyl with 1 to 6 fluorine atoms and
X represents oxygen or sulphur (preferably sulphur).

Particularly preferred compounds of the formula (I) are those in which
R represents hydrogen, $C_1$-$C_4$-alkyl, $C_3$-$C_6$-cycloalkyl, $C_1$-$C_4$-alkoxy, $C_1$-$C_4$-alkylthio, $C_1$-$C_4$-alkylamino, di-($C_1$-$C_4$)-alkylamino or phenyl,
$R^1$ represents $C_1$-$C_4$-alkyl,
$R^2$ represents trifluoromethyl, 2,2,2-trifluoroethyl, 2,2,3,3-tetrafluoropropyl or 1,1,1,3,3,3-hexafluoro-2-propyl and
X represents oxygen or sulphur (preferably sulphur), Especially preferred compounds of the formula (I) are those in which
R represents hydrogen, $C_1$-$C_4$-alkyl, cyclohexyl, methoxy, methylthio, i-propylthio, dimethylamino or diethylamino or phenyl,
$R^1$ represents methyl, ethyl or i-propyl,
$R^2$ represents 2,2,2-trifluoroethyl, 2,2,3,3-tetrafluoropropyl or 1,1,1,3,3,3-hexafluoro-2-propyl and
X represents oxygen or sulphur (preferably sulphur).

If, for example, O-ethyl-O-(2,2,2-trifluoroethyl)thionophosphoric acid diester-chloride and 5-hydroxy-2-phenyl-pyrimidine are used as starting substances for the process according to the invention, the corresponding reaction can be outlined by the following equation:

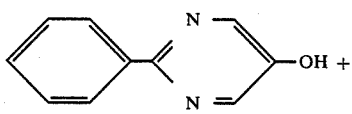

-continued

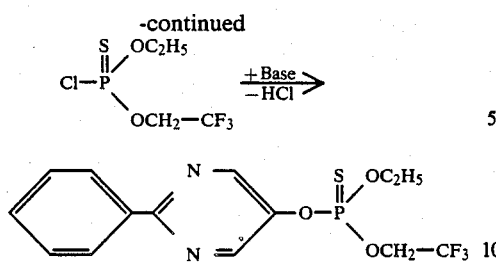

Formula (II) provides a definition of the 5-hydroxypyrimidines, or the corresponding alkali metal, alkaline earth metal or ammonium salts, to be employed as starting substances for the preparation of the new compounds of the formula (I) in the process according to the invention. In this formula, R represents those radicals which have been mentioned above in the definition in the case of formula (I). The sodium, potassium or calcium salts are preferably employed as the alkali metal or alkaline earth metal salts.

The compounds of the formula (II) are known and/or can be prepared by generally known processes and methods (compare, for example, DE-OS (German Published Specification) No. 2,643,262, DE-OS (German Published Specification) No. 2,706,127 and J. Chem. Soc. 1960, 4590).

Examples which may be mentioned of the compounds of the formula (II) are: 5-hydroxy-pyrimidine, 2-methyl-, 2-ethyl-, 2-n-propyl-, 2-i-propyl-, 2-n-butyl-, 2-i-butyl-, 2-sec.-butyl, 2-tert.-butyl-, 2-cyclopropyl-, 2-cyclobutyl-, 2-cyclopentyl-, 2-cyclohexyl-, 2-phenyl-, 2-methoxy-, 2-ethoxy-, 2-n-propoxy-, 2-i-propoxy, 2-n-butoxy-, 2-i-butoxy-, 2-sec.-butoxy-, 2-tert.-butoxy-, 2-methylthio-, 2-ethylthio-, 2n-propylthio-, 2-i-propylthio, 2-n-butylthio-, 2-i-butylthio, 2sec.-butylthio-, 2-tert.-butylthio-, 2-(di)methylamino-, 2-(di)ethylamino-, 2-(di)n-propylamino-, 2-(di)i-propylamino-, 2-(di)n-butylamino-, 2-sec.-butylamino- and 2-tert.-butylamino-5-hydroxypyrimidine and the corresponding sodium, potassium, calcium and ammonium salts.

Formula (III) provides a definition of the halides also to be employed as starting substances. In this formula, X, R¹ and R² represent those radicals which have been mentioned in the definition in the case of formula (I). Hal in this formula represents halogen, such as, in particular, chlorine or bromine.

The compounds of the formula (III) are new and the present invention also relates to them. They can be prepared in a simple manner by known methods, by a process in which dihalides of the formula (IV)

in which
R¹, X and Hal have the abovementioned meanings, are reacted with alcohols of the formula (V)

in which
R² has the abovementioned meaning,
in the presence of acid acceptors, such as, for example, collidine, N,N-dimethylaniline, dimethylbenzylamine, pyridine or triethylamine, and in the presence of inert diluents, such as, for example, toluene, at temperatures between −10° C. and +50° C., in approximately equimolar amounts.

The starting compounds of the formula (IV) are generally known compounds of organic chemistry.

Examples which may be mentioned of the compounds of the formula (IV) are: O-methyl-, O-ethyl-, O-n-propyl-, O-i-propyl-, O-n-butyl-, O-i-butyl-, O-sec.-butyl- and O-tert.-butyl-(thiono)phosphoric acid ester-dichloride and -dibromide.

The starting compounds of the formula (V) are generally known compounds of organic chemistry.

Examples which may be mentioned of the compounds of the formula (V) are: trifluoromethanol, difluoromethanol, 2,2,2-trifluoroethanol, 3,3,3-trifluoropropanol, 2,2,3,3-tetrafluoropropanol, 1,1,1,3,3,3-hexafluoropropan-2-ol, 3,3,3-trifluoro-propan-2-ol and 2,2,3,4,4,4-hexafluorobutan-1-ol.

Examples which may be mentioned of the halides of the formula (III) are: O-methyl-O-trifluoromethyl-, O-ethyl-O-trifluoromethyl-, O-n-propyl-O-trifluoromethyl-, O-i-propyl-O-trifluoromethyl-, O-n-butyl-O-trifluoromethyl-, O-i-butyl-O-trifluoromethyl-, O-sec.-butyl-O-trifluoromethyl-, O-tert.-butyl-O-trifluoromethyl-, O-methyl-O-difluoromethyl-, O-ethyl-O-difluoromethyl-, O-n-propyl-O-difluoromethyl-, O-i-propyl-O-difluoromethyl-, O-n-butyl-O-difluoromethyl-, O-i-butyl-O-difluoromethyl-, O-sec.-butyl-O-difluoromethyl-, O-tert.-butyl-O-difluoromethyl-, O-methyl-O-(2,2,2-trifluoroethyl)-, O-ethyl-O-(2,2,2-trifluoroethyl)-, O-n-propyl-O-(2,2,2-trifluoroethyl)-, O-i-propyl-O-(2,2,2-trifluoroethyl)-, O-n-butyl-O-(2,2,2-trifluoroethyl)-, O-i-butyl-O-(2,2,2-trifluoroethyl)-, O-sec.-butyl-O-(2,2,2-trifluoroethyl)-, O-tert.-butyl-O-(2,2,2-trifluoroethyl)-, O-methyl-O-(3,3,3-trifluoropropyl)-, O-ethyl-O-(3,3,3-trifluoropropyl)-, O-n-propyl-O-(3,3,3-trifluoropropyl)-, O-i-propyl-O-(3,3,3-trifluoropropyl)-, O-n-butyl-O-(3,3,3-trifluoropropyl)-, O-i-butyl-O-(3,3,3-trifluoropropyl)-, O-sec.-butyl-O-(3,3,3-trifluoropropyl)-, O-methyl-O-(2,2,3,3-tetrafluoropropyl)-, O-ethyl-O-(2,2,3,3-tetrafluoropropyl)-, O-n-propyl-O-(2,2,3,3-tetrafluoropropyl)-, O-i-propyl-O-(2,2,3,3-tetrafluoropropyl)-, O-n-butyl-O-(2,2,3,3-tetrafluoropropyl)-, O-i-butyl-O-(2,2,3,3-tetrafluoropropyl)-, O-sec.-butyl-O-(2,2,3,3-tetrafluoropropyl)-, O-methyl-O-(1,1,1,3,3,3-hexafluoro-2-propyl)-, O-ethyl-O-(1,1,1,3,3,3-hexafluoro-2-propyl)-, O-n-propyl-O-(1,1,1,3,3,3-hexafluoro-2-propyl)-, O-n-butyl-O-(1,1,1,3,3,3-hexafluoro-2-propyl)-, O-methyl-O-(3,3,3-trifluoro-2-propyl)-, O-ethyl-O-(3,3,3-trifluoro-2-propyl)-, O-n-propyl-O-(3,3,3-trifluoro-2-propyl)-, O-i-propyl-O-(3,3,3-trifluoro-2-propyl)-, O-n-butyl-O-(3,3,3-trifluoro-2-propyl)-, O-methyl-O-(2,2,3,4,4,4-hexafluoro-1-butyl)-, O-ethyl-O-(2,2,3,4,4,4-hexafluoro-1-butyl)-, O-n-propyl-O-(2,2,3,4,4,4-hexafluoro-1-butyl)-, O-i-propyl-O-(2,2,3,4,4,4-hexafluoro-1-butyl)-, O-n-butyl-O-(2,2,3,4,4,4-hexafluoro-1-butyl)-, O-i-butyl-O-(2,2,3,4,4,4-hexafluoro-1-butyl)-, O-sec.-butyl-O-(2,2,3,4,4,4-hexafluoro-1-butyl)- and O-tert.-butyl-O-(2,2,3,4,4,4-hexafluoro-1-butyl)-(thiono)phosphoric acid ester-chloride and -bromide.

The process according to the invention for the preparaton of the new pyrimidin-5-yl-thionophosphoric acid esters of the formula (I) is preferably carried out using diluents. Possible diluents are virtually all the inert organic solvents.

These include, in particular, aliphatic or aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylenesulphone and hexamethylphosphoric acid triamide.

If appropriate, the process can be carried out in the presence of acid acceptors. All the customary acid-binding agents can be used as acid acceptors. Acid-binding agents which have proved particularly suitable are alkali metal carbonates, such as sodium carbonate and potassium carbonate, and furthermore aliphatic, aromatic or heterocyclic amines, for example triethylamine, trimethylamine, dimethylaniline, dimethylbenzylamine and pyridine.

The process according to the invention is in general carried out at temperatures between 0° C. and 100° C. The range between 15° C. and 80° C. is preferred. The reactions are in general carried out under normal pressure.

For carrying out the process according to the invention, the starting substances are usually employed approximately in equimolar amounts. An excess of one or the other of the reaction components provides no substantial advantages. The reaction is in general carried out in a suitable diluent in the presence of an acid acceptor and the reaction mixture is stirred at the required temperature for several hours. Thereafter, an organic solvent, for example toluene, is added and the organic phase is worked up in the customary manner by washing, drying and distilling off the solvent.

The new compounds are obtained in the form of oils, some of which cannot be distilled without decomposition but can be freed from the last volatile constituents by so-called "incipient distillation", that is to say by prolonged heating to moderately elevated temperatures under reduced pressure, and can be purified in this manner. They are characterized by their refractive index.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example *Phylloxera vastatrix,* Pemphigus spp., *Pediculus humanus corporis, Haematopinus spp.* and *Linognathus spp.* From the order of the Mallophaga, for example, *Trichodectes spp.* and *Damalinea spp.* From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineta, Phaedon cochleariae,* Diabrotica spp., *Psylliodes chrysocephala, Epilachna varivestis,* Atomaria spp., *Oryzaephilus surinamensis,* Anthonomous spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster, Musca* spp., *Fannia spp., Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus,* Oscinella frit, Phorbia spp., *Pegomyia hyoscyami, Ceratitis capitata, Dacus oleae* and *Tipula paludosa.* From the order of the Siphonaptera, for examle, *Xenopsylla cheopis* and Ceratophyllus spp. From the order of the Arachnida, for example, *Scorpio maurus* and *Latrodectus mectans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp. and Trichodorus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocabons, such as chlorobenzenes, chlororethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocabons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating insects, mites, ticks and the like in the field of livestock husbandry and cattle breeding, it being possible to achieve better results, for example higher milk yields, a heavier weight, a more attractive animal coat, a longer life and the like, by combating the pests.

The active compounds according to the invention are used in this field in a known manner, such as by external use in the form of, for example, dipping, spraying, pouring on and spotting on and dusting.

As has already been mentioned above, the new compounds of the formula (I) are distinguished by a very low toxicity to warm-blooded animals. In contrast, the previously known highly active representatives of this type of compound have relatively high toxicity values which considerably impede their use in practice. The new compounds of the formula (I) show the high insecticidal and nematicidal activity of the already known compounds, but are many times superior to these in their lower toxicity to warm-blooded animals. Preparation, storage, formulation and use are thereby facilitated and simplified to a high degree. It was surprising and contrary to previous experience in expert circles that the new compounds of the formula (I) would show a low toxicity to warm-blooded animals without their insecticidal and nematicidal action being reduced. In fact, a substantial reduction in the insecticidal and nematicidal activities would have been expected.

The low toxicity of the new compounds of the formula (I) to warm-blooded animals and their high and broad activity against insects and nematodes may be illustrated with the aid of the following examples. The following highly active compounds known from DE-OS (German Published Specification) No. 2,643,262 and U.S. Pat. No. 4,429,125 were also included in the tests in some cases:

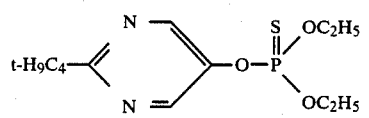
(A)

and

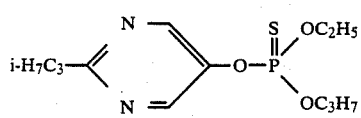
(B)

EXAMPLE A

Toxicity to warm-blooded animals, $LD_{50}$ values on rats (oral)

| Active compound | $LD_{50}$ (mg of active compound/ kg of body weight) |
|---|---|
| Comparison compound (A) | 1–2.5 |
| Compound from Preparation Example 1 | 100–250 |
| Compound from Preparation Example 2 | 50 |

The values were determined in the customary manner. The active compounds were dissolved in polyethylene glycol LUTROL (trademark of BASF AG, Ludwigshafen, Federal Republic of Germany) and the solution was administered to rats with a stomach tube.

EXAMPLE B

Critical concentration test/soil insects

Test insect: *Phorbia antiqua* maggots (in the soil)
Solvent: 3 parts by weight of acetone
Emulsifier: 1 part by weight alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effeciveness is 100% if all the test insects have been killed and is 0% if just as many test insects are still alive as in the case of the untreated control.

In this test, for example, the compounds according to the invention from preparation Examples 1 and 2 and the known compounds (A) and (B) show a degree of effectiveness of 95%; 100%; 100% and 100% at an active compound concentration of 2.5 ppm.

EXAMPLE C

Critical concentration test/soil insects

Test insect: *Diabrotica balteata* larvae in the soil
Solvent: 3 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The soil is filled into 0.5 liter pots and these are left to stand at 20° C.

Immediately after setting up the test, 6 pregerminated grains of corn are placed in each pot. After 2 days, the corresponding test insects are introduced into the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, compounds (1) and (2) according to the invention and the known compound (A) show a degree of effectiveness of 100% at an active compound concentration of 2.5 ppm.

EXAMPLE D

Critical concentraion test/nematodes

Test nematode: *Meloidogyne incognita*
Solvent: 3 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, lettuce is sown in and the pots are kept at a greenhouse temperature of 27° C.

After four weeks, the lettuce roots are examined for infestation with nematodes (root galls), and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, compounds (1) and (2) according to the invention and the known compounds (A) and (B) show a degree of effectiveness of 95%, 100%, 100% and 95% at an active compound concentration of 20 ppm.

EXAMPLE E

Test with *Lucilia cuprina* OP res. larvae

Emulsifier:
35 parts by weight of ethylene glycol monoethyl ether
35 parts by weight of nonylphenol polyglycol ether.

To produce a suitable preparation of active compound, three parts by weight of active compound are mixed with seven parts by weight of the abovementioned solvent mixture and the concentrate thus obtained is diluted with water to the particular desired concentration.

About 20 *Lucilia cuprina* res. larvae are introduced into a test tube which contains approx. 1 cm² of horse muscle and 0.5 ml of the preparation of active compound. After 24 hours, the degree of destruction is determined.

In this test, for example, compound (2) shows a destruction of 100% at an active compound concentration of 10 ppm.

EXAMPLE F

Test with *Psoroptes ovis*

Solvent:
35 parts by weight of ethylene glycol monomethyl ether
35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the desired concentration.

About 10–25 *Psoroptes ovis* are introduced into 1 ml of the active compound preparation to be tested, this having been pipetted into tablet nests of a deep-drawn package. After 24 hours, the degree of destruction is determined.

In this test, for example, compound (2) shows a destruction of 100% at an active compound concentration of 10 ppm.

PREPARATION EXAMPLES

Example 1

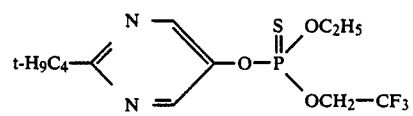

A mixture of 7.8 g (0.05 mole) of 2-tert.-butyl-5-hydroxypyrimidine, 10.4 g (0.075 mole) of potassium carbonate, 50 ml of acetonitrile and 12.2 g (0.05 mole) of O-ethyl-O-(2,2,2-trifluoroethyl)-thionophosphoric acid diester-chloride is stirred at 20° C. for 18 hours. After addition of 150 ml of toluene, the mixture is extracted 3 times with 100 ml of water each time. The organic phase is then dried over sodium sulphate and the solvent is distilled off in vacuo. The residue is subjected to incipient distillation in vacuo at 80° C.

12.5 g (70% of theory) of O-ethyl O-(2,2,2-trifluoroethyl) O-(2-tert.-butyl-pyrimidin-5-yl)thionophosphate remain in the form of a yellow oil with the refractive index $n_D^{21} = 1.4819$.

The following compounds of the formula (I)

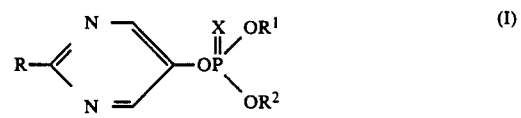

can be prepared analogously to Example 1:

| Example No. | R | R¹ | R² | X | Refractive index |
|---|---|---|---|---|---|
| 2 | t-C₄H₉ | C₂H₅ | CHF₂—CF₂—CH₂— | S | $n_D^{22}$: 1.4640 |
| 3 | t-C₄H₉ | i-C₃H₇ | CF₃—CH₂— | S | $n_D^{22}$: 1.4652 |
| 4 | t-C₄H₉ | i-C₃H₇ | CHF₂—CF₂—CH₂— | S | $n_D^{22}$: 1.4657 |
| 5 | H | C₂H₅ | CF₃—CH₂— | S | |
| 6 | CH₃ | C₂H₅ | CF₃—CH₂— | S | |
| 7 | ▷— | C₂H₅ | CF₃—CH₂— | S | $n_D^{22}$: 1.4775 |
| 8 | i-C₃H₇ | C₂H₅ | CF₃—CH₂— | S | |

-continued

| Example No. | R | R¹ | R² | X | Refractive index |
|---|---|---|---|---|---|
| 9 | (cyclohexyl-H) | $C_2H_5$ | $CF_3-CH_2-$ | S | |
| 10 | (phenyl) | $C_2H_5$ | $CF_3-CH_2-$ | S | $n_D^{22}$: 1.5630 |
| 11 | $t-C_4H_9$ | $C_2H_5$ | $CF_3-CH_2-$ | O | $n_D^{22}$: 1.4470 |
| 12 | $t-C_4H_9$ | $C_2H_5$ | $CHF_2-CF_2-CH_2-$ | O | $n_D^{22}$: 1.4384 |
| 13 | 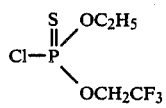 | $i-C_3H_7$ | $CHF_2-CF_2-CH_2-$ | S | |
| 14 | $t-C_4H_9$ | $CH_3$ | $CF_3-CH_2-$ | S | |
| 15 | $t-C_4H_9$ | $CH_3$ | $CHF_2-CF_2-CH_2-$ | S | |
| 16 | $t-C_4H_9$ | $C_2H_5$ | $(CF_3)_2CH-$ | S | |
| 17 | $SCH_3$ | $C_2H_5$ | $CF_3-CH_2-$ | S | |
| 18 | $OCH_3$ | $C_2H_5$ | $CF_3-CH_2-$ | S | |
| 19 | $SC_3H_7-i$ | $C_2H_5$ | $CF_2-CH_2-$ | S | |
| 20 | $N(CH_3)_2$ | $C_2H_5$ | $CF_3-CH_2-$ | S | |
| 21 | $N(CH_3)_2$ | $C_2H_5$ | $CHF_2-CF_2-CH_2-$ | S | |
| 22 | $N(C_2H_5)_2$ | $C_2H_5$ | $CF_3-CH_2-$ | S | |
| 23 | (phenyl) | $C_2H_5$ | $CHF_2-CF_2-CH_2-$ | S | $n_D^{22}$: 1.5300 |
| 24 | (cyclohexyl-H) | $C_2H_5$ | $CHF_2-CF_2-CH_2-$ | S | |
| 25 | $i-C_3H_7$ | $C_2H_5$ | $CHF_2-CF_2-CH_2-$ | S | |
| 26 | $t-C_4H_9$ | $n-C_3H_7$ | $CF_3-CH_2-$ | S | |

Starting substances of the formula (III)

Example (III-1)

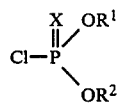

A mixture of 60.5 g (0.5 mole) of collidine and 50 g (0.5 mole) of 2,2,2-trifluoroethanol is added dropwise to a solution of 89.5 g (0.5 mole) of O-ethyl-thionophosphoric acid ester-dichloride in 300 ml of toluene at 15°–20° C., with gentle cooling. The reaction mixture is subsequently stirred at 20° C. for 24 hours, washed with 100 ml of water and then with 100 ml of 2 percent strength hydrochloric acid and three times with 100 ml of water each time, dried over sodium sulphate and evaporated in vacuo.

75.8 g (62% of theory) of O-ethyl-O-(2,2,2-trifluoroethyl)-thionophosphoric acid diester-chloride are thus obtained in the form of a colorless oil with a boiling point of 62°–64° C./11 mbar.

The following compounds of the formula (III)

$$\underset{Cl-P}{\overset{X}{\|}}\underset{OR^2}{\overset{OR^1}{/}} \quad (III)$$

can be prepared analogously to Example (III-1):

| Example No. | R¹ | R² | X | Physical constants |
|---|---|---|---|---|
| III-2 | $C_2H_5$ | $CHF_2-CF_2-CH_2-$ | S | Boiling point: 46–49° C./0.01 mbar |
| III-3 | $i-C_3H_7$ | $CF_3-CH_2-$ | S | Boiling point: 68° C./14 mbar |
| III-4 | $CH_3$ | $CF_3-CH_2-$ | S | |
| III-5 | $C_2H_5$ | $CF_3-CH_2-$ | O | |
| III-6 | $C_2H_5$ | $(CF_3)_2CH-$ | S | |
| III-7 | $n-C_3H_7$ | $CF_3-CH_2-$ | S | |
| III-8 | $i-C_3H_7$ | $CHF_2-CF_2-CH_2-$ | S | $n_D^{21}$: 1.4486 |

It will be understood that the specification and examples are illustrative but not limitative of the present invention and that other embodiments within the spirit and scope of the invention will suggest themselves to those skilled in the art.

We claim:

1. A pyrimidin-5-yl-thionophosphoric acid ester of the formula

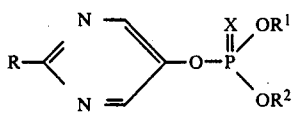

in which

R represents hydrogen, or represents $C_1$–$C_6$-alkyl, $C_3$–$C_6$-cycloalkyl, $C_1$–$C_6$-alkoxy, $C_1$–$C_6$-alkylthio, $C_1$–$C_6$-alkylamino, di-($C_1$–$C_4$-alkyl)amino or phenyl, $R^1$ represents $C_1$–$C_6$-alkyl, $R^2$ represents fluoro-$C_1$–$C_6$-alkyl with 1 to 6 fluorine atoms, and X represents oxygen or sulphur.

2. A compound according to claim 1, in which

R represents hydrogen, $C_1$–$C_4$-alkyl, $C_3$–$C_6$-cycloalkyl, $C_1$–$C_4$-alkoxy, $C_1$–$C_4$-alkylthio, $C_1$–$C_4$-alkylamino, di($C_1$–$C_4$)-alkylamino or phenyl, $R^1$ represents $C_1$–$C_4$-alkyl, and $R^2$ represents trifluoromethyl, 2,2,2-trifluoroethyl, 2,2,3,3-tetrafluoropropyl or 1,1,1,3,3,3-hexafluoro-2-propyl.

3. A compound according to claim 1, in which

R represents hydrogen, $C_1$–$C_4$-alkyl, cyclohexyl, methoxy, methylthio, i-propylthio, dimethylamino or diethylamino or phenyl, $R^1$ represents methyl, ethyl or i-propyl, $R^2$ represents 2,2,2-trifluoroethyl, 2,2,3,3-tetrafluoropropyl or 1,1,1,3,3,3-hexafluoro-2-propyl and X represents sulphur.

4. A compound according to claim 1 wherein such compound is O-ethyl O-(2,2,2-trifluoroethyl) O-(2-tert.-butyl-pyrimidin-5-yl)thionophosphate of the formula

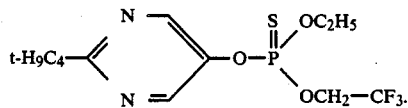

5. A compound according to claim 1 wherein such compound is O-ethyl O-(2,2,3,3-tetrafluoropropyl) O-(2-tert.-butyl-pyrimidin-5-yl)thionophosphate of the formula

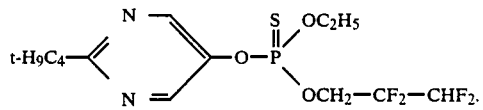

6. A compound according to claim 1 wherein such compound is O-isopropyl O-(2,2,2-trifluoroethyl) O-(2-tert.-butyl-pyrimidin-5-yl)thionophosphate of the formula

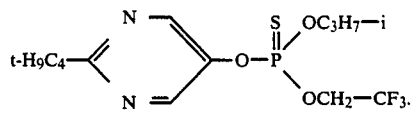

7. A compound according to claim 1 wherein such compound is O-isopropyl O-(2,2,3,3-tetrafluoropropyl) O-(2-tert.-butyl-pyrimidin-5-yl)thionophosphate of the formula

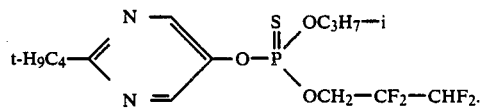

8. A compound according to claim 1 wherein such compound is O-ethyl O-(2,2,2-trifluoroethyl) O-(2-cyclopropyl-pyrimidin-5-yl)thionophosphate of the formula

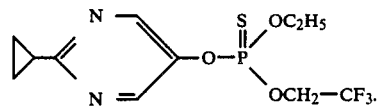

9. An insecticidal or nematicidal composition comprising an insecticidally or nematicidally effective amount of a compound according to claim 1 and a diluent.

10. A method of combating insects or nematodes which comprises applying to such insects or nematodes or to a habitat thereof an insecticidally or nematicidally effective amount of a compound according to claim 1.

11. The method according to claim 10 wherein such compound is:

O-ethyl O-(2,2,2-trifluoroethyl) O-(2-tert.-butyl-pyrimidin-5-yl)thionophosphate, O-ethyl O-(2,2,3,3-tetrafluoropropyl) O-(2-tert.-butyl-pyrimidin-5-yl)thionophosphate, O-isopropyl O-(2,2,2-trifluoroethyl) O-(2-tert. butyl-pyrimidin-5-yl)thionophosphate, O-isopropyl O-(2,2,3,3-tetrafluoropropyl) O-(2-tert.-butyl-pyrimidin-5-yl)thionophosphate or O-ethyl O-(2,2,2-trifluoroethyl) O-(2-cyclopropyl-pyrimidin-5-yl)thionophosphate.